US006255540B1

(12) United States Patent
Erhardt et al.

(10) Patent No.: US 6,255,540 B1
(45) Date of Patent: Jul. 3, 2001

(54) METHODS FOR PRODUCING TWO-SUBSTITUTED GLYCEROLS HAVING VARIOUS LEVELS OF PROTECTION

(75) Inventors: Paul W. Erhardt, Sylvania; Wieslaw A. Klis, Toledo, both of OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 09/605,440

(22) Filed: Jun. 28, 2000

Related U.S. Application Data
(60) Provisional application No. 60/141,694, filed on Jun. 30, 1999.

(51) Int. Cl.$^7$ ................................................. C07C 31/18
(52) U.S. Cl. ........................... 568/853; 568/852; 568/866; 435/7.1; 435/DIG. 50
(58) Field of Search .................................. 568/853, 852, 568/866

(56) References Cited

U.S. PATENT DOCUMENTS 4,483,978   11/1984   Manser .

OTHER PUBLICATIONS

Sharma, Rajiv; Lee, Jeewoo; Wang, Shaomeng; Milne, George W.A.; Lewin, Nancy E.; Blumberg, Peter M.; Marquez, Victor E.; Conformationally Constrained Analogues of Diacylglycerol. 10. Ultrapotent Protein Kinase C Ligands Based on a Racemic 5–Disubstituted Tetrahydro–2–furanone Template, J.Med.Chem. (1996), 39, pp. 19–28.
Lee, Jeewoo; Wang, Shaomeng; Milne, George W.A.; Sharma, Rajiv; Lewin, Nancy E.; Blumberg, Peter M.; Marquez, Victor E.; Conformationally Constrained Analogues of Diacylglycerol. 11. Ultrapotent Protein Kinase C Ligands Based on a Chiral 5–Disubstituted Tetrahydro–2–furanone Template, J.Med.Chem. (1996), 39, pp. 29–35.
Lee, Jeewoo; Lewin, Nancy E.; Acs, Peter; Blumberg, Peter M.; Marquez, Victor E.; Conformationally Constrained Analogues of Diacylglycerol. 13. Protein Kinase C Ligands Based on Templates Derived from 2,3–Dideoxy–L–erythro–(threo)–hexono–1,4–lactone and 2–Deoxyapiolactone, J. Med. Chem. (1996), 39, pp. 4912–4919.
Erhardt, Paul W.; In Pursuit of a Microtubule Binding Site, Taxane Journal (May 1997), vol. 111, No. 1, pp. 36–40.
Chen, Shu–Hui; Huang, Stella; Wei, Jianmei; Farina, Vittorio; The Chemistry of Taxanes: Reaction of Taxol and Baccatin Derivatives with Lewis Acids in Aprotic and Protic Media, Tetrahedron (1993), vol. 49, No. 14, pp. 2805–2806.
Macias, Francisco, A.; Molinillo, Jose Maria G.; Massanet, Guillermo M.; First Synthesis of Two Naturally Occurring Oxetone Lactones: Clementein and Clementein B, Tetrahedron (1993), vol. 49, No. 12, pp. 2499–2508.
Collado, Isidro G.; Macias, Francisco A.; Massanet, Guillermo M.; Molinillo, Jose Maria G.; –Luis, Francisco R.; Chemical Transformation of Deacylsubexpinnatin into the Natural Oxetane Lactone Subexpinnatin C, J.Org.Chem. (1987), 52, pp. 3323–3326.
Holton, Robert A.; Somoza, Carmen; Kim, Hyeong–Baik; Liang, Feng; Biediger, Ronald J.; Boatman, P. Douglas; Shindo, Mitsura; Smith, Chase C.; Kim, Soekchan; Nadizadeh, Hossain; Suzuki, Yukio; Tao, Chunlin; Vu, Phong; Tang, Suhan; Zhang, Pingsheng; Murthi, Krishna K.; Gentile, Lisa N.; Liu, Jyanwei H.; The Total Synthesis of Paclitaxel Starting with Camphor, American Chemical Society (1995), pp. 288–301.
Holton, Robert A.; Somoza, Carmen; Kim, Hyeong–Baik; Liang, Feng; Biediger, Ronald J.; Boatman, P. Douglas; Shindo, Mitsuru; Smith, Chase C.; Kim, Soekchan; Nadizadeh, Hossain; Suzuki, Yukio; Tao, Chunlin; Vu, Phong; Tang, Suhan; Zhang, Pingsheng; Murthi, Krishna K.; Gentile, Lisa N.; Liu, Jyanwei H.; First Total Synthesis of Taxol. 1. Functionalization of the B Ring, J.Am.Chem.Soc. (1994), 116, pp. 1597–1598.
Holton, Robert A.; Kim, Hyeong–Baik; Somoza, Carmen; Liang, Feng; Biediger, Ronald J.; Boatman, P. Douglas; Shindo, Mitsuru; Smith, Chase C.; Kim, Soekchan; Nadizadeh, Hossain; Suzuki, Yukio; Tao, Chunlin; Vu, Phong; Tang, Suhan; Zhang, Pingsheng; Murthi, Krishna K.; Gentile, Lisa N.; Liu, Jyanwei H.; First Total Synthesis of Taxol. 2. Completion of the C and D Rings, J.Am.Chem.Soc. (1994), 116, pp. 1599–1600.
Rubottom, George M.; Gruber, John M.; Juve, Jr., Henrik D.; Charleson, Dan A.; α–Hydroxy Ketones from the Oxidation of Emol Silyl Ethers with m–Chloroperbenzoic Acid: 6–Hydroxy–3,5,5–Timethyl–2–Cyclohexen–1–One, Org. Synth. (1986), vol. 64, pp. 118–126.
Yorozu, Kiyotaka; Takai, Toshihiro; Yamada, Tohru; Mukaiyama, Teruaki; A Novel Method for the Preparation of Acid–Sensitive Epoxides from Olefins with the Combined Use of Molecular Oxygen and Aldoacetal Catalyzed by a Cobalt(II) Complex, Bull.Chem.Soc.Jpn. (Aug. 1994), 67, pp. 2195–2202.

(List continued on next page.)

*Primary Examiner*—Johann Richter
*Assistant Examiner*—Elvis O Price
(74) *Attorney, Agent, or Firm*—Emch, Schaffer, Schaub & Porcello Co., L.P.A.

(57) ABSTRACT

A method for producing 2-substituted glycerols having various levels of hydroxy group protection by opening dihydroxyacetone dimer in a nonaqueous, non-protic environment with a composition that initially protects both of the liberated 1,3-dihydroxy groups to form di-ether containing ketone monomers which can then be conveniently subjected to ketone addition reactions and standard chemical functional group manipulations.

26 Claims, 7 Drawing Sheets

OTHER PUBLICATIONS

Eliel, Ernest L.; Freeman, Jeremiah P.; The Mechanism of Halide Reductions with Lithium Aluminum Hydride. II. Reduction of 2–Chloro–2–phenylpropionic Acid, J.Am.Chem.Soc. (1952), vol. 74, pp. 923–928.

Gupton, John T.; Durancaue, Steven J.; Miller, John F.; Kosiba, Michael L.; The Reaction of α–Methylstyrene Analogs and Related Compounds With Sodium Perborate in Acetic Acid, Synthetic Communications (1988), 18(9), pp. 937–947.

Burgess, Edward M.; Penton, Jr., Harold R.; Taylor, E.A.; Thermal Reactions of Alkyl N–Carbomethoxysulfamate Esters, J.Org.Chem. (1973), vol. 38, No. 1, pp. 26–31.

Monson, Richard S.; Priest, Deggary N.; Dehydration of Secondary Alcohols by Hexamethylphosphoric Triamide, J.Org. Chem. (1971), vol. 36, No. 24, p. 3826.

Traynelis, Vincent J.; Hergenrother, William L.; Livington, Joel R.; Valicenti, John A.; Dehydration of Alcohols in Dimethyl Sulfoxide, J.Org.Chem. (Jul. 1962), vol. 27, pp. 2377–2383.

Goodall, Matthew; Kelly, Patricia M.; Parker, David; Gloe, Karsten; Stephan, Holger; Selective Cation Binding with cis, cis–1,3,5 Trioxycyclohexyl based ligands: Application to Ion Transport and Electrochemical Detection and Assessment of Complexation of Electrospray Mass Spectrometry, J.Chem.Soc.Perkin Trans.2 (1997), pp. 59–69.

Corey, E.J.; Snider, Barry B.; A Total Synthesis of ±–Fumagillin, J.Am.Chem.Soc. (1972), 94, pp. 2549–2550.

Pikul, S.; Corey, E.J.; Enantioselective, Catalytic Diels–Alder Reaction: (1S–endo)–3–(Bicyclo[2.2.1] Hept–5–en–2–Ylcarbonyl)–2–Oxazolidinone, Org.Synth. (1993), vol. 71, pp. 30–33.

Lee, Jeewoo; Sharma, Rajiv; Wang, Shaomeng; Milne, George W.A.; Lewin, Nancy E.; Szallasi, Zoltan; Blumberg, Peter M.; George, Clifford; Marquez, Victor E.; Conformationally Constrained Analogues of Diacylglycerol. 12. Ultrapotent Protein Kinase C Ligands Based on a Chira 4,4–Disubstituted Heptono–1,4–lactone Template, J.Med. Chem. (1996), 39, pp. 36–45.

Marchand, Alan P.; Wang, Yanjun; Ren, Chien–tai; Vidyasagar, Vuligonda; Wang, Dongqing; On the Mechanism of Acid Promoted Ring Opening of a Pentacyclo[$5.4.0.0^{2,6}.0^{3,10}.0^{5,9}$]undecane–Spiroannulated Oxetane, Tetrahedron (1996), vol. 52, No. 17, pp. 6063–6072.

Oyumi, Yoshio; Inokami, Kiyotaka; Yamazaki, Kazuhiro; Matsumoto, Koki; Thermal Decomposition of BAMO/HMX Propellants, Pyrotech. (1993), 18, pp. 62–68.

Prior Art Figure 1

Key: (a) LDA/TMSCl; (b) mClPBA; (c) TMSCl/Triethylamine; (d) MeMgBr/Ether; (e) RCl; (f) Burgess Reagent; (g) OsO$_4$; (h) Hydrolysis. Dotted arrows indicated planned reactions that were not completed.

Prior Art Figure 2

Key: (a) $NaBO_3$/AcOH; (b) DMSO; (c) $NaBO_3$, AcOH; (d) NaOH.

Prior Art Figure 3

Key: (a) AcOK/AcOH; (b) MePPH$_3$Br/t-BuOK; (c) NMO/OsO$_4$; (d) NaOMe.

Key: 5 = 1,3-Dihydroxyacetone dimer; (a) TMSCl/Triethylamine; (b) RMgBr/Ether/$H_3O^{\oplus}$. For the case were R = $\emptyset$, a 70% overall yield is obtained.

Key: 5 = 1,3-Dihydroxyacetone dimer; (a) TMSCl/Triethylamine; (b) RMgBr/Ether or NaCN or BrCHR$^1$CO$_2$R$^2$/Zn or R$^3$CH$_2$NO$_2$ wherein none of the addition reaction possibilities utilize an aq. Acid wash; (c) ØCH$_2$Br/NaH or ØCH$_2$Br/Aq.K$_2$CO$_3$/Crown Ether wherein either method also utilizes an aq. Acid wash during workup.

Figure 6

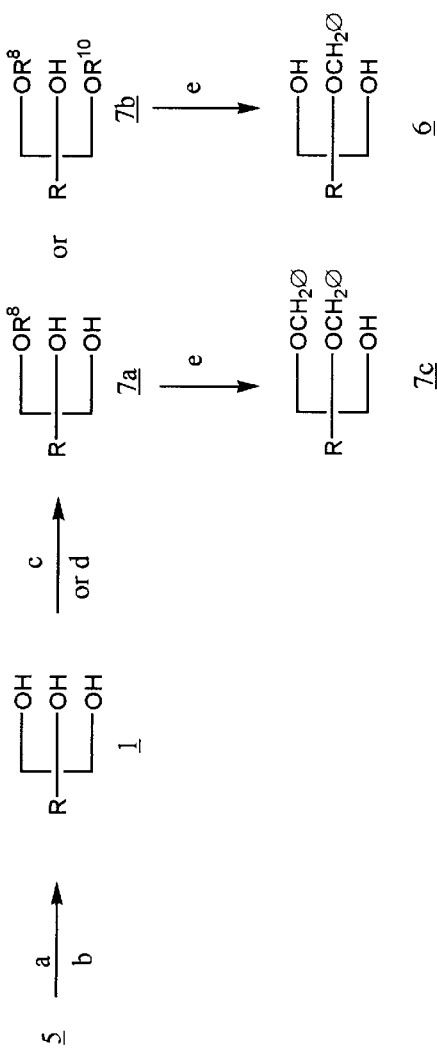

Key: 5 = 1,3-Dihydroxyacetone dimer; (a) TMSCl/Triethylamine; (b) RMgBr/Ether or NaCN or BrCHR$^1$CO$_2$R$^2$/Zn or R$^3$CH$_2$NO$_2$ wherein an acidic wash is utilized during the workup. (c) One equivalent of an alkylating or an acylating agent system; (d) Two equivalents of an alkylating or an acylating agent system; (e) For the case when R$^8$ in 7a is an acyl group, treatment with two equivalents of ØCH$_2$Br/NaH followed by aqueous NaOH produces the 1,2-diprotected material 7c whereas for the case when R$^8$ and R$^{10}$ in 7b are acyl groups, treatment with one equivalent of ØCH$_2$Br/NaH followed by aqueous NaOH provides an alternate pathway to 6.

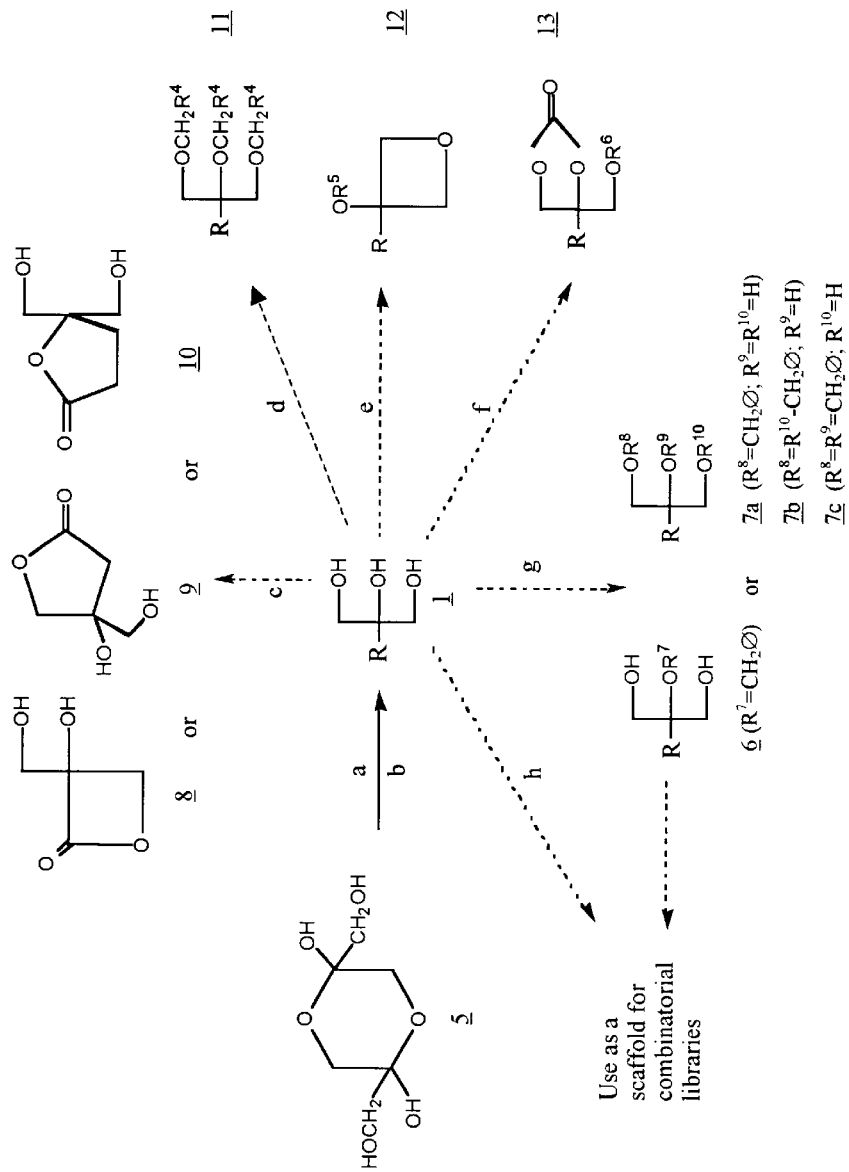

Figure 7

Key: $\underline{5}$ = 1,3-Dihydroxyacetone dimer; Reaction path a plus b show the inventive methodology leading to $\underline{1}$. Dotted lines depict chemical application s of $\underline{1}$ based upon analogy to well-established, synthetic literature methods. The exact chemical nature of R" where n=4 to 8 will depend upon the particular interest in using a given target type and is independent of the inventive chemical steps a plus b. See text for additional details.

METHODS FOR PRODUCING TWO-SUBSTITUTED GLYCEROLS HAVING VARIOUS LEVELS OF PROTECTION

This application claim benefit to provisional application 60/141,694 Jun. 30, 1999.

BACKGROUND OF THE INVENTION

Glycerol derivatives represent useful synthetic building blocks toward a variety of compounds that are of interest for pure and applied chemical investigations as well as for the development of commercially significant manufacturing processes. For example, as part of an applied program within the pharmaceutical arena to define structure-activity relationships associated with the anticancer drug paclitaxel (Erhardt, P. W. Taxane Journal 1997, 3, 36) there is a need for a ready and inexpensive synthesis of 2-phenylglycerol, 1 as shown below where R=Ø.

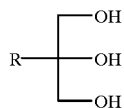

Specifically, the inventors and others have been trying to define the role that might be played by the 3-acetoxyoxetane system within paclitaxel toward producing the latter's beneficial anticancer properties (Chen, S.-H.; Huang, S.; Wei, J.; Farina, V. Tetrahedron 1993, 49, 2805). This oxetane system is a distinctive molecular arrangement (Macias, F. A.; Molinillo, J. M. G.; Massanet, G. M. Tetrahedron 1993, 49, 2499) that, along with its potential formation within the novel context of 2-phenylglycerol, takes on considerable interest from a chemical manufacturing point of view (Collado, I. G.; Macias, F. A.; Massanet, G. M.; Molinillo, J. M. G.; R.-Luis, F., J. Org. Chem. 1987, 52, 3323 and Holton, R. A.; Somoza, C.; Kim, H.-B.; Liang, F.; Biedeger, R. J.; Boatman, P. D.; Shindo, M.; Smith, C. C.; Kim, S.; Nadizadeh, H.; Suzuki, Y.; Tao, C.; Vu, P.; Tang, S.; Zhang, P.; Murthi, K. K.; Gentile, L. N.; Liu, J. H. Taxane Anticancer Agents Basic Science and Current Status, 288; Georg, G. I.; Chen, T. T.; Ojima, I.; Vyas, D. M., Eds.; American Chemical Society: Washington, D.C., 1995).

Anticipating a ring closure similar to that developed by Holton et al., 1994 during their total synthesis of paclitaxel, (Holton, R. A.; Somoza, C.; Kim, H. B.; Liang, F.; Biedeger, R. J.; Boatman, P. D.; Shindo, M.; Smith, C. C.; Kim, S.; Nadizadeh, H.; Suzuki, Y.; Tao, C.; Vu, P.; Tang, S.; Zhang, P.; Murthi, K. K.; Gentile, L. N.; Liu, J. H. J. Am. Chem. Soc. 1994, 116, 1597 and Holton, R. A.; Kim, H. B.; Somoza, C.; Liang, F.; Biedeger, R. J.; Boatman, P. D.; Shindo, M.; Smith, C. C.; Kim, S.; Nadizadeh, H.; Suzuki, Y.; Tao, C.; Vu, P.; Tang, S.; Zhang, P.; Murthi, K. K.; Gentile, L. N.; Liu, J. H. J. Am. Chem. Soc. 1994, 116, 1599) the inventors initially deployed acetophenone, 2, according to FIG. 1 as the most inexpensive and directly analogous starting material appropriate for producing 2-phenylglycerol, 1 where R=Ø, which could then be used as the key building block for further elaboration into the desired oxetanes. Toward this end, the enol form of acetophenone, 2, was trapped as its trimethylsilyl (TMS) ether (Step a) (Rubottom, G. M.; Gruber, J. M.; Juve, Jr., H. D.; Charleson, D. A. Org. Synth. 1986, 64, 118) which was vacuum distilled (42–43° C., 0.10 mm Hg) prior to its oxidation with meta-chloroperbenzoic acid (Step b) to produce α-hydroxyacetophenone. In addition to having appropriate NMR spectroscopic data, crystallization of the latter from hexane/ethyl acetate (1/1) provided material having a melting point of 88–90° C. which is comparable to the technical literature (Yorozu, K.; Takai, T.; Yamada, T.; Mukaiyama, T. Bull Chem. Soc. Jpn. 1994, 67, 2195: melting point=87 to 89° C.) as well as to commercial grade specifications (Aldrich Chem. Co.: melting point=86 to 89° C. and Acros Organics/Fisher Scientific: melting point=86 to 88° C.). Formation of the TMS ether (Step c) followed by immediate reaction with methylmagnesium bromide (Step d) then produced racemic 1,2-dihydroxy-2-phenylpropane. Flash chromatography and crystallization of the latter from hexane/ether (1/1) provided material again having appropriate NMR data and a melting point of 43–45° C. which is comparable to both the technical literature and commercial grade specifications (Eliel, E. L.; Freeman, J. P. J. Am. Chem. Soc. 1952, 74, 923: melting point=44 to 45° C. and Aldrich Chem. Co.: mp=44 to 45° C., respectively). However, at this point the overall yield for just the first four steps of this eight-step strategy had already plummeted to less than 20%. Thus, a higher yielding and more expedient pathway to compound 1 was sought and the latter steps of this first approach, as shown by dotted lines in FIG. 1, were not pursued.

Expediting the synthesis by deploying α-methylstyrene, 3, as an equally inexpensive and appropriate starting material was tried next according to the scheme depicted in FIG. 2. Starting material 3 was gently oxidized by using sodium perborate ($NaBO_3$) in acetic acid (Step a) to produce 1,2-dihydroxy-2-phenylpropane whose 1-position hydroxyl group was simultaneously protected via an acetyl function when the procedure was conducted according to Gupton, et al. 1988 (Gupton, J. T.; Duranceau, S. J.; Miller, J. F.; Kosiba, M. L. Synth. Comm. 1988, 18, 937). Purification of the initial material from this reaction was accomplished by vacuum distillation in a range (96–98° C., 0.25 mm Hg) similar to that specified within the technical literature (Gupton et al. 1988) to provide a high quality product in about 40% yield. This is itself a significant improvement since this product corresponds to the same type of intermediate that would have been obtained after five steps (Steps a through e) according to the previous strategy as shown in FIG. 1. Dehydration of the tertiary alcohol (Step b in FIG. 2) with either Burgess reagent (Burgess, E. M.; Penton, Jr., H. R.; Taylor, E. A. J. Org. Chem. 1993, 58, 26) or hexamethylphosphoramide (Monson, R. S.; Priest, D. N. J. Org. Chem. 1971, 36, 3826) proved less effective than by simply heating the material at 165° C. in DMSO for 10 hours (Traynelis, V. J.; Hergentrother, W. L.; Livingston, J. R.; Valicenti, J. A. J. Org. Chem. 1962, 27, 2377). Purification by vacuum distillation (60–66° C., 0.05 mm Hg) was less effective than by flash silica gel column chromatography eluted with toluene to provide a material of acceptable quality (appropriate NMR spectrum with no extraneous peaks) in about a 50% yield. Oxidation was then smoothly effected by again utilizing $NaBO_3$ in acetic acid (Step c), this time affording a mixture of the mono- and di-acetylated primary alcohol versions of the desired 2-phenylglycerol in about 35% yield. Although these materials were readily separable by flash silica gel column chromatography when eluted with hexane/ethyl acetate (1/1), they tended to reform mixtures even when stored at 2 to 3° C. This propensity for acylated glycerols to readily undergo isomerization by trans-esterification processes is also exemplified by diacylglycerol which is sold by Aldrich Chemical Co. under the name 'Diacetin' as a mixture of the 1,2-, the 1,3- and the 1,2,3- di- and triacetylglycerols. Therefore, upon repetitions of the method shown in FIG. 2, the mixed products from the second $NaBO_3$ oxidation reaction were directly subjected to hydrolysis using 1 N NaOH in methanol (Step d). Purification could then be much more effectively accomplished by crystallization from $CH_2Cl_2/CCl_4$ (3/1) to provide the final product 2-phenylglycerol, 1 with R=Ø, in about a 70% yield for the final step and in about a 5% overall yield for the entire four-step procedure. Complete physical property specifications for 2-phenylglycerol are provided in the Examples Section.

Simultaneous with our investigations, FIG. 3 depicts a very similar four-step process to produce 2-phenylglycerol that was recently reported by Goodall et al. 1997 (Goodall M.; Kelly, P. M.; Parker, D.; Gloe, K.; Stephan, H. *J. Chem. Soc. Perkin Trans.* 2 1997, 59). However, this strategy deploys the more expensive α-bromoacetophenone, 4, as the starting material to arrive at the same substituted styrene intermediate similarly obtained after two steps within FIG. 2. Furthermore, $OsO_4$ is then utilized for the oxidation followed by sodium methoxide for the hydrolysis, both reagents being far less practical from a manufacturing point of view than those deployed in FIG. 2 to effect these same types of conversions. Nevertheless, the reported overall yield in the Goodall et al. case is nearly 30%.

Continuing to explore synthetic strategies that might provide 2-substituted glycerol materials in an even more expeditious and higher yielding manner while still keeping the costs down, we have now discovered that 1,3-dihydroxyacetone can be subjected to an addition reaction scheme, such as that afforded by a simple Grignard reaction, so as to produce 2-substituted glycerols with a broad range of substituent possibilities. Thus, according to the present invention, a novel, two-step strategy, as shown by FIG. 4, can be used to very conveniently obtain 2-phenylglycerol in nearly 70% yield after deploying the inexpensive dimer of 1,3-dihydroxyacetone as the starting material.

SUMMARY OF THE INVENTION

The present invention relates to the convenient and inexpensive production of 2-substituted glycerols having various levels of hydroxy-group protection. The substituents can be either alkyl, aryl or carboxyl wherein the alkyl or aryl substituents can also bear additional chemical functionalities, provided that when the additional chemical functionalities are themselves reactive, then they are masked at least during portions of the production process by appropriate protecting groups.

According to the first aspect of the present invention, 1,3-dihydroxyacetone dimer is opened by treatment with an ether forming reagent system such as trimethylsilyl chloride (TMSCl) plus triethylamine, in a non-aqueous, non-protic solvent such as dichloromethane (DCM) to provide the monomeric ketone having both of its alcohols protected as their ethers, e.g. as their TMS ethers. The latter is then subjected to an addition reaction with either a Grignard reagent, (RMgX where X=halide such as Br) a cyanate reagent (NaCN), a Reformatsky substrate ($BrCHR^1CO_2R^2$), or an appropriate nitroalkane system ($R^3CH_2NO_2$). The chemical work-up after the addition reaction is then carried out in a manner that intentionally unmasks the protected alcohols, such as by inclusion of an acidic wash for removal of TMS ethers, so as to directly provide the 2-substituted glycerol derivative in a completely unprotected form. This aspect of the invention is shown in FIG. 4 for the specific case where the addition reaction utilizes a common Grignard reagent and the 2-substituent is a phenyl ring, 1 wherein R=Ø.

According to a second aspect of the present invention, 1,3-dihydroxyacetone dimer is opened and subjected to an addition reaction as described above but is then worked-up in a manner that initially preserves the TMS-protected alcohols (avoidance of acidic conditions). Since this particular form of the protected glycerol 2-substituted derivatives does not lend itself to extensive purification, it is deployed in a partially purified state so as to allow for selective reaction at the free 2-hydroxyl function. For example, reaction with benylbromide may be done at this juncture by employing either sodium hydride under anhydrous conditions or potassium carbonate in a two phase system that also contains a Crown ether to help the various chemical species traverse the two phases. Chemical work-up that now includes an acidic wash then provides the 2-substituted glycerol derivative that also has its 2-position hydroxy-group protected as a benzyl ether. This monoprotected form is quite stable and lends itself to further, complete purification. This aspect of the invention is shown in FIG. 5 with the described modification leading to the mono-protected compound 6 rather than to compound 1.

According to a third aspect of the present invention, 1,3-dihydroxyacetone dimmer is initially opened and subjected to an addition reaction followed by a workup involving an acidic wash exactly as described in the first inventive aspect. Subsequent deployment of this material can then allow for preferential reaction at either the 1-positon or at the 1- and 3-position primary alcohols compared to the 2-position tertiary alcohol by using either one equivalent or two equivalents of an alkylating or acylating reagent system, respectively. For example, reaction with one or two equivalents of benzylbromide may be done at this juncture by employing one or two equivalents of sodium hydride under anhydrous conditions to provide the 2-substituted glycerols with their 1-hydroxyl or their 1- and 3-hydroxyl groups protected as their benzyl or dibenzyl ethers, respectively. Likewise, reaction with one or two equivalents of benzoylchloride in the presence of an acid scavenger in an organic solvent such as pyridine in toluene may be done at this juncture to provide the 2-substituted glycerols with their 1-hydroxyl or their 1- and 3-hydroxyl groups protected as their benzoyl esters, respectively. In the case of the monoester protected materials, it was also found that the 1-benzoyl-2-substituted glycerols could be further reacted with two equivalents of sodium hydride and two equivalents of benzylbromide followed by an aqueous sodium hydroxide workup to provide 2-substituted glycerols with both their 1- and 2-position hydroxyl groups protected as their benzyl ethers. Similarly, in the case of the diester-protected materials, it was found that the 1,3-dibenzoyl-2-substituted glycerols could be further reacted with one equivalent of sodium hydride and one equivalent of benzylbromide followed by an aqueous sodium hydroxide workup to provide 2-substituted glycerols with just their 2-hydroxyl group positions protected as their benzyl ethers. Thus, the latter represents an alternative pathway for producing the same types of 2-substituted, 2-benzyl-protected glycerols such as 6 that were described in the second aspect of the present invention. The variations of this aspect of the invention are depicted in FIG. 6 with the resulting 1-oxygen, the 1,3-dioxygen, and the 1,2-dioxygen protected systems depicted as compounds 7a, 7b, and 7c, respectively.

Finally, according to a fourth aspect of this invention, the chemical sequences depicted in FIGS. 4, 5 and 6 can be similarly traversed by deploying mixtures of ketone addition reagents wherein the R substituent of RMgX, the $R^1$ and $R^2$ substituents of $BrCHR^1CO_2R^2$ or the $R^3$ substituent of $R^3CH_2NO_2$ can all be varied so as to represent a series of chemical species that are then simultaneously utilized as a mixture within the reaction rather than as single reagents. In this aspect of the invention, the methods conveyed in FIGS. 4, 5 and 6 produce combinatorial libraries of products while compounds 1, 6 and 7 respectively represent scaffolds for each of such combinatorial series rather than representing a single chemical entity in each case.

DESCRIPTION OF THE FIGURES

FIG. 6 shows a novel multi-step process for producing 2-substituted glycerols protected at either the 1-oxygen position, at the 1,3-dioxygen positions, or at the 1,2-dioxygen positions.

FIG. 7 shows how the inventive method can be readily directed down several different paths for further using 2-substituted glycerols like 1 to produce a variety of useful chemical and commercially significant structures.

DESCRIPTION OF THE INVENTION

Figure 1:
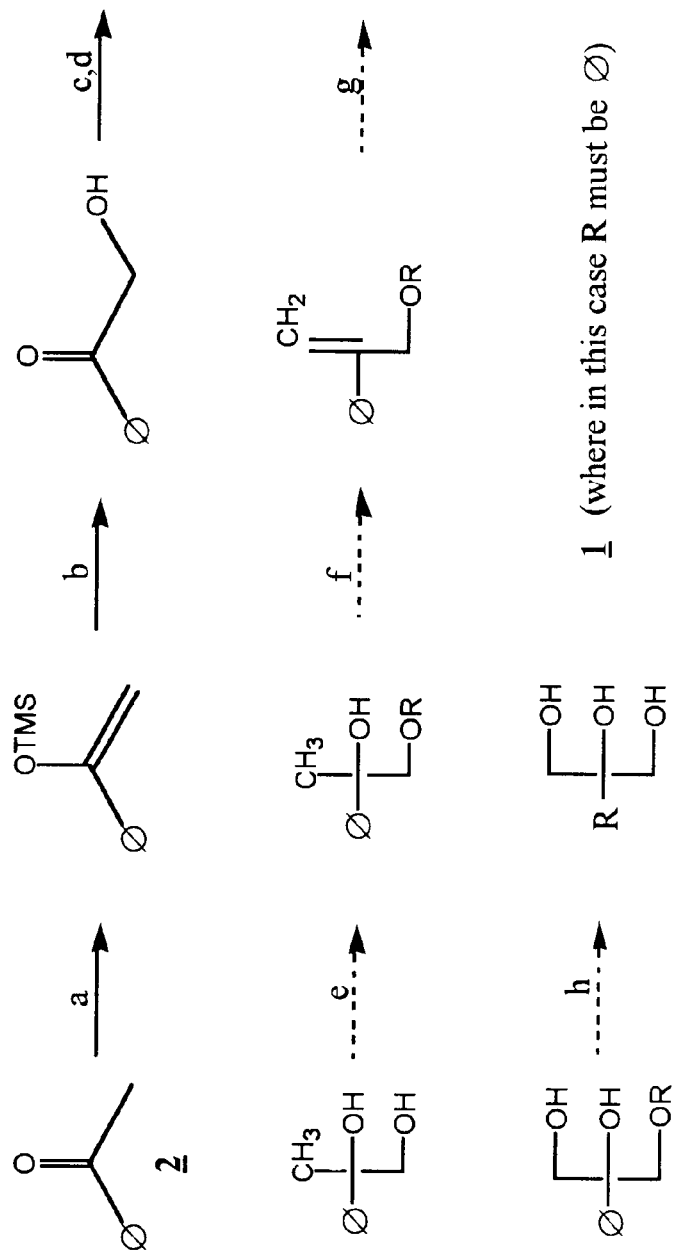
FIG. 1 shows a scheme for the synthesis of 2-phenylglycerol based upon close prior art.
Figure 2:
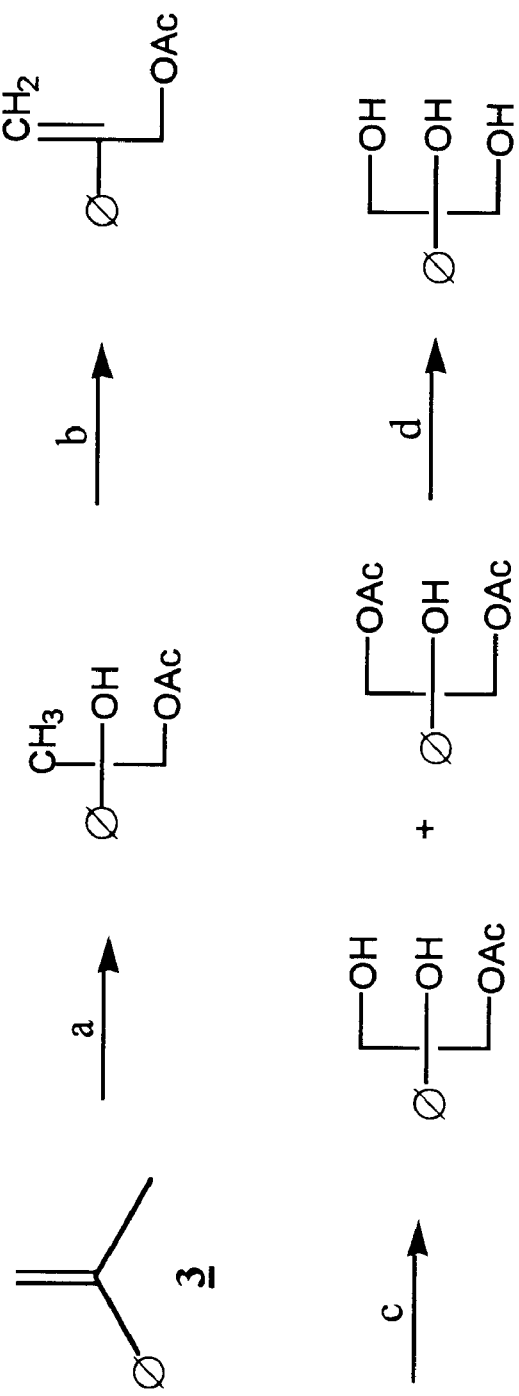
FIG. 2 shows another scheme for the synthesis of 2-phenylglycerol based upon the combination of established prior art.
Figure 3:
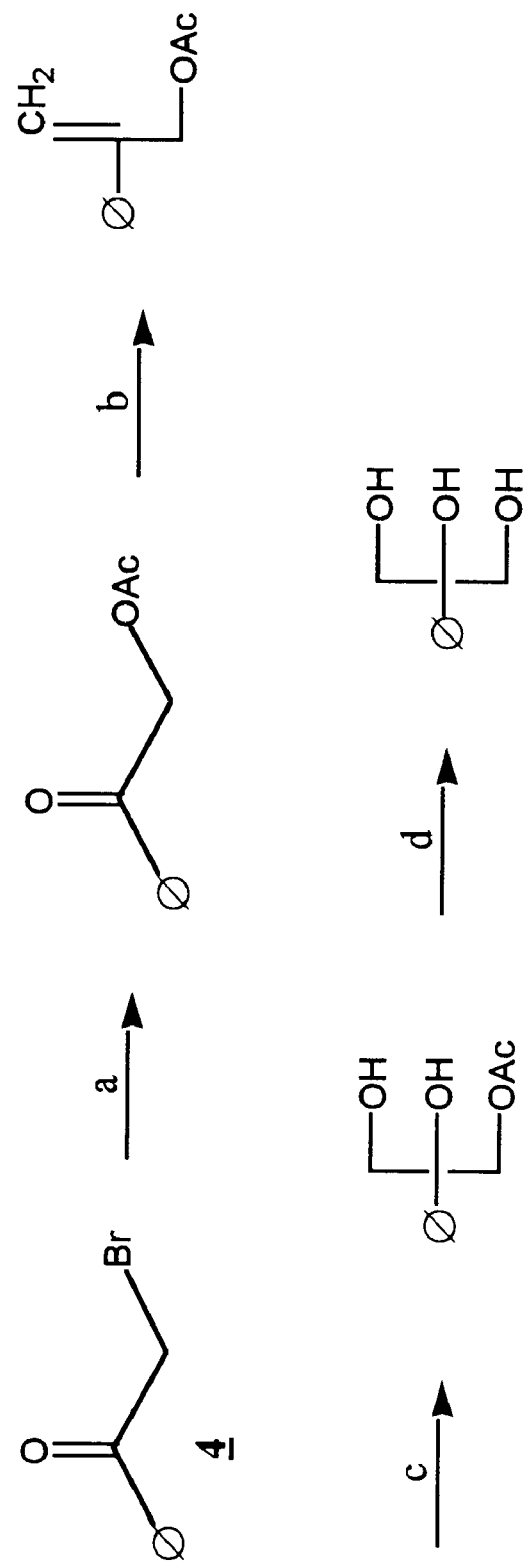
FIG. 3 shows a recently published scheme for the synthesis of 2-phenylglycerol that is analogous to the method of FIG. 2.
Figure 4:
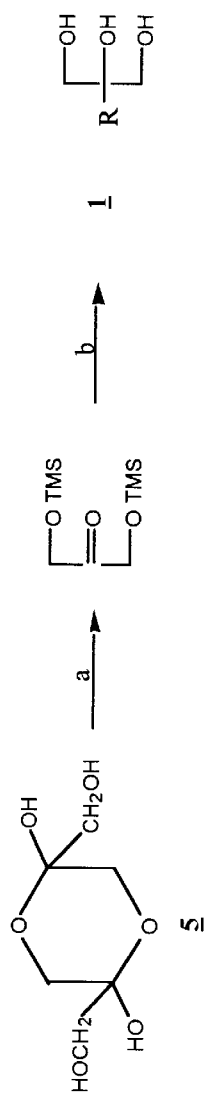
FIG. 4 depicts the overall invention's novel approach for a two-step synthesis of 2-substituted glycerols within the specific context of the 2-phenylglycerol target compound.

Referring now to FIG. 4, the overall method of the present invention is generally shown within the context of the specific and previously difficult synthetic case that demonstrates the new method's clear superiority over the prior art as described in the Background Section. TMSCl plus triethylamine can be readily utilized to open the inexpensive dihydroxyacetone dimer within a nonaqueous, non-protic environment while simultaneously protecting both of the so-liberated 1,3-dihydroxy groups (Corey E. J.; Snider, B. B. *J. Am. Chem. Soc.* 1972, 94, 2549 provides a general reference to the use of TMS protecting groups) such that the resulting di-TMS ether containing ketone monomers are strategically well-suited to undergo addition reactions. Reaction with a phenylmagnesium bromide Grignard reagent is illustrative of such an addition reaction and when this reaction is worked-up with saturated aqueous ammonium chloride (Pikul, S.; Corey, E. J. *Org. Synth.* 1993, 71, 30) followed by an acidic partitioning step using 2 N HCl so as to intentionally prompt cleavage of the TMS ethers, 2-phenylglycerol, 1 R=Ø, is produced in an overall two-step procedure that requires only filtration and drying between the two steps. The overall yield for this extremely facile procedure from inexpensive starting materials approaches 70%, more than double that of all prior methods.

It is to be noted that other reagent systems deployed along this route of synthesis failed to produce isolable 2-substituted glycerols. One set of reagents which was tried initially used ester-forming rather than ether-forming protecting groups to open the dihydroxyacetone. However, hydrolysis during work-up of the Grignard reaction occurred and no product could be readily obtained from the paired reactions. Another method attempted to use either mesyl or tosyl intermediates and in these cases only uncharacterized resinous materials were retrieved upon work-up. Yet another approach attempted to use carbonate type protecting groups which ultimately produced cyclic carbonates across neighboring hydroxy groups when arriving at the product stage.

Figure 5:
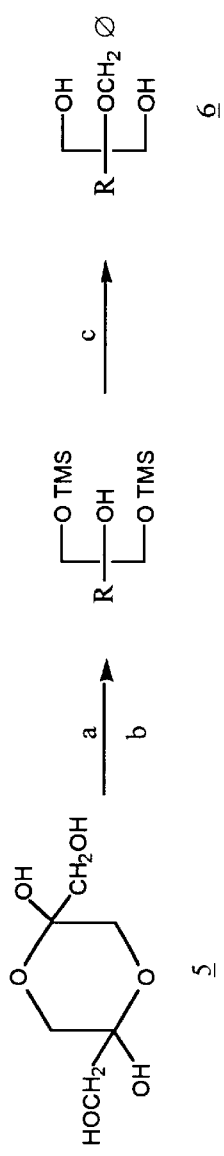
FIG. 5 shows a novel three-step process for producing 2-substituted, 2-oxygen-protected glycerol derivatives.

Referring now to FIGS. 5 and 6, subtle modifications and extensions of the overall method are specifically shown to allow for the production of the 2-substituted glycerols to be obtained as either the 2- or 1-position oxygen mono-protected forms or as the 1,3- or 1,2-dioxygen, di-protected systems. For example, by avoiding the acidic partitioning step during initial work-up and instead subjecting the partially purified intermediate to reaction with benzylbromide followed by an acidic treatment, mono-protected compounds such as 6 can be obtained. If benzoyl esters are placed on 1 followed by reaction with benzylbromide and then cleaved, either mono- or di-protected ether compounds such as 7 can be obtained as the final 2-substituted glycerol protected products.

FIG. 7 again depicts the overall method of the present invention, namely steps (a) and (b). However, FIG. 7 also shows various avenues for the further practical application and further commercialization of the inventive method as exemplified by steps (c), (d), (e), (f), (g) and (h). In particular, FIG. 7 shows the synthesis of 2-substituted glycerol, 1, from 1,2-dihydroxyacetone dimer, 5, and its conversion to a variety of compositions of potential commercial interest. As before, (a) involves treatment with TMSCl plus triethylamine in an organic solvent and (b) involves an addition reaction with either a Grignard reagent (RMgX) or any of its closely-related chemical addition species, a cyanate reagent (NaCN), a Reformatsky substrate $BrCHR^1CO_2R^2$) plus Zn, or finally a nitroalkane system ($R^3CH_2NO_2$) plus base, with each of these addition reaction possibilities being conducted in an organic solvent.

As is then shown in FIG. 7, the method of the present invention becomes useful in producing various substituted glycerols such as certain conformationally constrained analogues of diacylglycerol that are of interest as anticancer agents (Lee, J.; Sharma, R,; Wang, S.; Milne, G. W. A; Lewin, N. E.; Szallasi, Z.; Blumberg, P. M.; George, C.; Marquez, V. E. *J. Med. Chem.*, 1996, 39, 36). Three of these templates which bear a 2-substituted glycerol pattern are shown as structures 8, 9 and 10 in FIG. 7. Compounds such as lactones 8 and 9 can be obtained directly via intramolecular cyclization of a cyanate reagent addition product and a Refromatsky addition product, respectively, whereas compounds such as lactone 10 require the use of an appropriately protected functional group-containing Grignard reagent during Steps a plus b followed by its unmasking prior to an analogous intramolecular cyclization to the lactone (Step c). These cyclization and functional group manipulations can be conducted by using any of several well-established methods. Thus, with the present invention's Steps a plus b described herein, all of the conversions needed to accomplish the aforementioned syntheses to 8, 9 and 10 can now be readily undertaken according to FIG. 7 by an individual who is reasonably skilled in the art.

Another use of the methods and compositions of the present invention is that of producing new ionophores for use in the measurement of intracellular or extracellular cation concentration, a subject of considerable current interest (Goodall et al. 1997) where 2-substituted glycerols are considered to represent good molecular templates from which to develop such biochemical reagents. A specific example of an agent of this type is shown in FIG. 7 as compound 11 wherein $R^4$ is a common cation chelating moiety. Compounds 11 are easily obtained from 1 by ether formation via standard chemical reactions (Step d) with a variety of commonly available chemical reagents having the general formula $R^4CH_2X$ where X is a typical leaving group moiety. Thus, with the present invention's Steps a plus b described herein, all of the conversions needed to produce compounds like 11 can again be readily undertaken according to FIG. 7 by an individual who is reasonably skilled in the art.

As discussed in the Background Section, a more chemically sophisticated example that demonstrates the utility of the inventive methods and materials related to 1 is for their further application toward preparing difficult to obtain oxetane analogues. In some cases the latter are, themselves, of commercial interest as anticancer or anti-infective agents while in other cases investigators have utilized oxetane system chemistry during the synthesis of a variety of natural products having an even wider range of therapeutic applications (Collado, I. G.; Macias, F. A.; Massanet, G. M.; Molinillo, J. M. G.; and Luis, F. R.; *J. Org. Chem.* 1987, 52, 3323, and Macias, F. A.; Molinillo, J. M. G.; and Massanet, G. M. *Tetrahedron,* 1993, 49, 2499). Oxetane chemistry is of additional commercial relevance outside the life sciences arena. For example, interest has been expressed in the use of oxetane-derived polymers as binders in solid gun propellants and as key components of cast-cured explosives (Manser, G. E. U.S. Pat. No. 4,483,978 (1985) and Oyumi, Y.; Inokami, K.; Yarnazaki, K. and Matsomoto, K. *Pyrotech,* 1993, 18, 62 and Marchand, A. P.; Wang, Y.; Ren, C.; Vidyasagar, V. and Wang, D, *Tetrahedron,* 1996, 52, 6063). A 2-substituted oxetane system is depicted as structure 12 in FIG. 7. Compounds such as 12 can be obtained from 1 by: (i) protection of the tertiary alcohol as, for example, an ether with $R^5$ in order to avoid formation of an oxirane due to cyclization of adjacent hydroxy positions; (ii) conversion of either one of the two chemically identical primary alcohols to a leaving group system; and (iii) ring closure to the oxetane as shown to proceed down Step e toward 12. While the formation of oxetanes does not represent trivial chemistry, the ready availability of 1 as afforded by the inventive process described herein will certainly assist this difficult area of synthetic constructions. It can also be noted that the first inventive modification of the overall method that produces compound 6 according to FIG. 5 provides the exact type of tertiary hydroxy group protection that is needed for 1 within FIG. 7 as cited above for (i) wherein $R^4$ then conveniently becomes a standard benzyl-protecting group. Again, the ready availability of this type of intermediate having the chemical rigor particularly afforded by the benzyl ether, that is now just two steps (ii and iii) away from an oxetane system should assist even further toward subsequently achieving these types of difficult chemistries.

Production of various cyclic carbonates represents yet another utility for using compounds such as 1 with the latter being readily produced by the methods described in the present invention. Carbonates such as those illustrated by compound 13 in FIG. 7 can have interesting pharmaceutical properties themselves, as for example by their structural resemblance to the earlier mentioned lactones 8, 9 and 10 which, in turn, are of interest as anticancer agents. Alternatively, the carbonates can serve as carrier or depot systems for other pharmaceutically active molecules when their chemistry is coupled with drug delivery technologies. Compounds such as 13 can be obtained by reacting 1 with common carbonate type protecting groups because we have found that the initial intermediates will subsequently undergo ready, spontaneous cyclization (Step f). For example, treatment of 1 with IBOCCl plus pyridine followed by reaction with benzylbromide using NaH for proton abstraction readily provides 13 where $R^6$ is benzyl.

Various 2-substituted glycerols having a tertiary-hydroxy-oxygen-$R^7$ moiety wherein $R^7$ is a protecting group, can be obtained from isolated 1. Note that when $R^7$ is a benzyl group, as is specifically depicted by Step g within FIG. 7, then the resulting system is identical to 6, a specific compound which can also be obtained directly by the subtle modification of the invention as delineated in FIG. 5 without the need for isolating 1. Nevertheless, as shown in FIGS. 6 and 7, the benzyl-version 6 can also be obtained from isolated 1 via this more general method by treatment with two equivalents of an acylating reagent immediately followed by a standard reaction with benzylbromide and then standard deprotection of the acyl groups. Likewise, the mono- and di-protected forms obtained via the scheme shown in FIG. 6 and as represented in that case by 7a or b, can also be obtained from isolated 1 upon treatment with one or two equivalents of a benzylhalide ($R^8X$) and one or two equivalents of a suitable proton abstraction reagent according to standard synthetic practices. Compound 7c can also be obtained according to FIG. 6.

Finally, compounds such as 1, 6 and 7 by virtue of their selectively exposed hydroxy-groups, can be conveniently deployed (Step h) as scaffolds from which to further build combinatorial libraries according to the synthetic art that is evolving in this rapidly growing area. In this regard, such libraries could be built upon single compound versions of 1, 6 or 7 wherein R is a single specified substituent, or upon preliminary libraries of 1, 6 or 7 wherein R is a pre-selected mixture of chemically-related substituents produced according to the methods specified herein within the fourth aspect of the inventive process.

It is to be understood that for all representations of R across all of the depicted and discussed compounds and in particular for compounds 1, 6, 7 and their further elaborated materials, R can comprise carboxyl ($CO_2H$) except when located on MgX, alkyl ($C_1$ to $C_{20}$), substituted alkyl, alkene ($C_2$ to $C_{20}$), substituted alkene, aryl, aralkyl ($C_7$ to $C_{25}$) and substituted aralkyl, where the substituent groups are either compatible with the reaction conditions (ethers or tertiary amines) or can be further protected so as to be compatible with the inventive reaction conditions (alcohols, primary and secondary amines typically requiring such protection to avoid reactivity). It is further understood that aryl includes heteroaromatic systems having one or more heteroatoms within one or more fused ring arrangements and that such systems can also be further substituted with unreactive or protected reactive groups. Also within this context, it is to be understood that all of the specifications for R except that of carboxyl (—$CO_2H$) extend to the cases $R^n$ where n=1 to 3. Finally, it is to be understood that when asymmetry is present within the protective groups, within the addition reaction reagents or within the materials resulting from the inventive process, all pure stereochemical isomer and stereochemical mixture possibilities whether enantiomeric, racemic or diastereomeric, are included within the scope of the chemical specifications as laid out herein.

The compounds shown below serve to exemplify various types of systems which are obtainable from the inventive steps a plus b as described herein. This list is not meant to be inclusive. Within this list, an asterisk denotes that the reactive chemical functionality depicted on a particular glycerol 2-positon R-side chain would have been protected during the addition reaction via standard functional group protection chemistry that is common to the art of chemical synthesis.

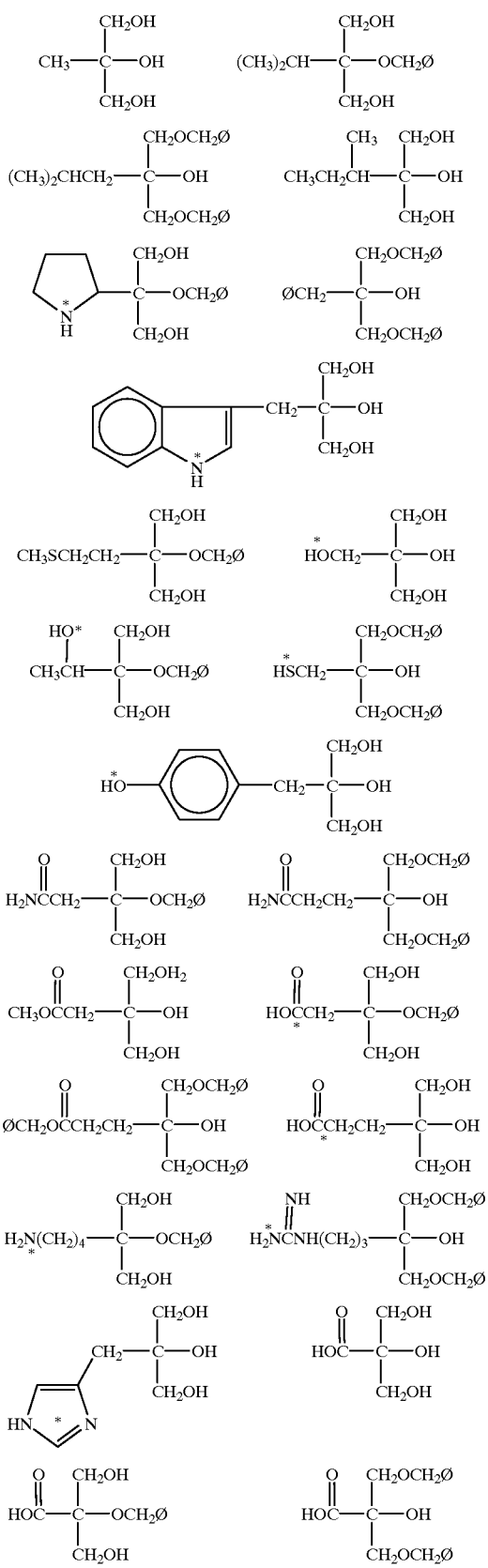

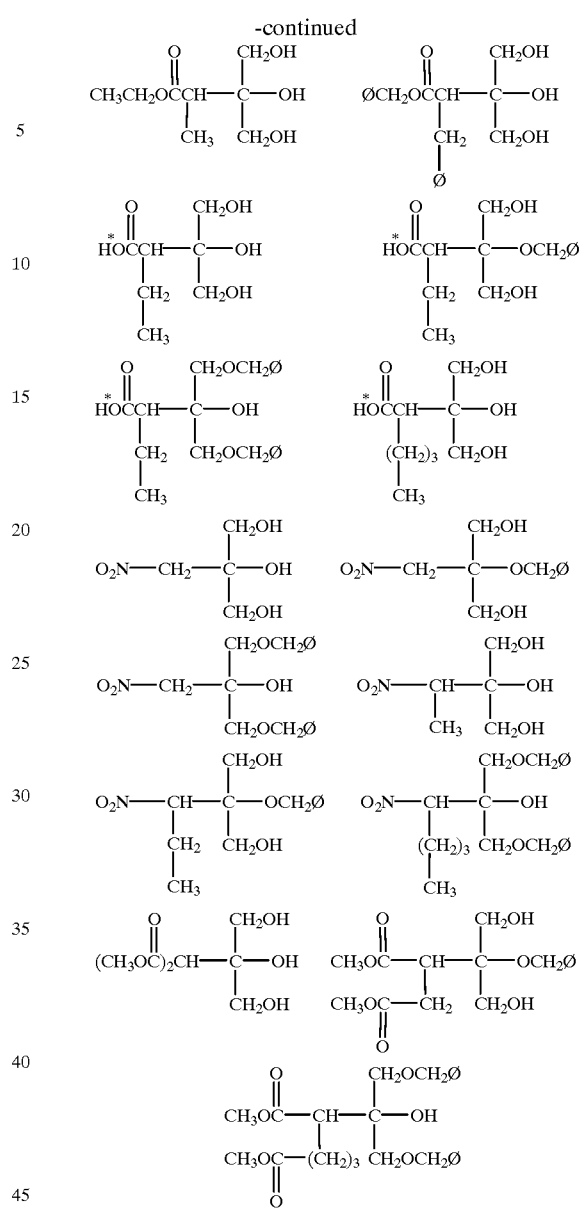

EXAMPLES

Organic solvents (anhydrous ether, carbon tetrachloride, dichloromethane, ethyl acetate, hexane, toluene) and reagents (3 M phenylmagnesium bromide in ether, triethylamine, trimethylsilyl chloride) were used as received from Aldrich Chemical Co. Starting material (dihydroxyacetone dimer) was used as received from Lancaster Synthesis Inc. or from Fisher Scientific. Aqueous solutions (saturated ammonium chloride, 2 N HCl, saturated NaCl) were prepared from their respective inorganic reagents as received from J. T. Baker Inc. Dry nitrogen gas was used as received from AGA Gas Co., Toledo, Ohio. Reactions were stirred magnetically and cooling was achieved by using dry ice/acetone baths. Organic phases were dried over anhydrous magnesium sulfate or potassium carbonate (J. T. Baker reagent grade) and brought to 2 to 3° C. prior to filtering. Evaporation of solvents was accomplished on a Buchi rotary evaporator connected to a water aspirator for reduced pressure. Drying of materials within desiccators was done at ambient temperature and pressure or at low vacuum pressure, employing Drierite/Indicating Drierite and sodium hydroxide purchased from Fisher Scientific. TLC was conducted by using Whatman silica bound to polyester-backed fluorescent indicator (F254) plates purchased from Fisher Scientific. Gravity column chromatography was conducted by using 60–200 mesh silica gel purchased from J. T. Baker Inc. Melting points were determined on an Electrothermal digital melting point apparatus and are uncorrected. Proton NMR spectra were recorded at 30° C. on a Bruker ACF 300-MHz fourier transform spectrometer in $CDCl_3$ (Cambridge Isotope Laboratories, Inc.) using residual solvent signal as the internal standard (7.26). IR spectra were recorded at ambient temperature on a Perkin Elmer model 1600 FT-IR Spectrophotometer using 3M type 62 IR cards purchased from Aldrich Chemical Co. Elemental analyses were performed by Atlantic Microlab Inc., Norcross, Ga.

2-Phenyl-1,2,3-trihydroxypropane (2-phenylglycerol) (1 R=Ø). Dihydroxyacetone dimer (3.6g, 20 mmol) was suspended in 20 mL of toluene and the toluene evaporated. Another 20 mL of toluene was added and evaporated followed by a similar addition and evaporation using 40 mL of dichloromethane (DCM). The residue was suspended in 80 mL of DCM and stirred at ambient temperature while 18 mL (130 mmol) of triethylamine as added. Trimethylsilyl chloride (14.8 g=17.2 mL, 136 mmol) was then added slowly over the course of 15 min via an addition funnel such that the reaction medium did not surpass a very gentle boil. After the addition, stirring was continued for another 3 h. The resulting dark purple solution was filtered and evaporated to provide a residue which was resuspended in 30 mL DCM, filtered and again evaporated. The dried residue was taken up in 20 mL of DCM and the solution dried over potassium carbonate prior to its filtration into an addition funnel. The flask used to dissolve the dried residue and the filtering set up where quickly rinsed with an additional 5 mL of cold DCM to produce a total volume within the addition funnel of approximately 25 mL DCM plus the monomeric ketone having both of its hydroxy groups now protected as their TMS ethers. The addition funnel was fitted to a round bottom flask also having a nitrogen glass flow system, a condenser and a thermometer port. The entire system was flushed with nitrogen gas and the round bottom flask charged with 20 mL of 3 M PhMgBr in ether (60 mmol). The flask was cooled, a continuous flow of nitrogen gas established, and then the contents of the addition funnel were slowly added over the course of 30 min. After the addition, the cooling bath was removed so that the reaction medium could gradually attain ambient temperature (ca. 2 h). The reaction was heated to reflux for 2 h and then left at room temperature overnight (ca. 15 h). A saturated aqueous solution of ammonium chloride (50 mL) was added dropwise and the mixture stirred for 15 min. The organic layer was separated and the aqueous layer extracted with 25 mL of ethyl acetate. The organic phases were combined, washed with 25 mL of saturated aqueous sodium chloride, treated with 50 mL of 2N HCl by partitioning and separation, and washed again with 25 mL of saturated aqueous sodium chloride. The combined aqueous phases were extracted with 50 mL of ethyl acetate. The organic phases were combined (ca. 125 mL), dried over magnesium sulfate and evaporated. The residue was taken up in warm ethyl acetate and purified by column chromatography (ca. 100 g Si) using hexane/ethyl acetate (1/2) as eluent. Fractions corresponding to $R_f$=0.15 when assessed by TLC (Si, hexane/ethyl acetate at 1/1) were combined and evaporated. Crystallization was achieved from DCM/carbon tetrachloride (ca. 5/1) to produce 4.42 g (66%) of white crystals having 0.4 mol ratio $H_2O$ after drying in a desiccator under low vacuum: mp 64 to 65° C. (lit. mp 44 to 46° C. for a non-hydrated solid obtained after evaporation of solvent); $^1$H NMR 1.69 (ca. 0.75 $H_2O$), 2.48 (s, 2H), 3.57 (s, 1H), 3.78–3.98 (m, 4H), 7.26–7.50 (m, 5H);IR ca. 3300 $cm^{-1}$ (brd). Anal. Calcd for $C_9H_{12}O_3$•0.4 $H_2O$: C, 61.63; H, 7.36. Found: C, 61.79; H, 7.34. In addition to the higher melting point observed for the hydrated crystals, x-ray diffraction studies have confirmed that 1 molecule of $H_2O$ packs between two molecules of 2-phenylglycerol indicating that this water is an inherent component of the unit cell within this particular crystalline species.

2-Phenyl-1,3-dibenzoyloxy-2-hydroxypropane (7b $R^8=R^{10}$=COØ). 2-Phenylglycerol (1.01 g, 6 mmol) was dissolved in 40 mL of DCM plus 5 mL of pyridine and the solution cooled via an ice bath (0–2° C.). Benzoylchloride (1.69 g or 1.4 mL, 12 mmol) in 5 mL of DCM was added dropwise. The reaction mixture was stirred overnight and allowed to gradually reach room temperature (ca. 15 hrs, ca. 20° C.). Another 0.5 mL (4 mmol) of benzoylchloride was added directly and the reaction stirred for another hour after which a TLC indicated the absence of both starting material and the monobenzoylated intermediate. The reaction medium was partitioned twice with 2N HCl (2×5 mL) and twice with water (2×5 mL), dried over anhydrous magnesium sulfate and evaporated under reduced pressure. The residue was taken up in 20 mL of ethyl acetate, treated with 180 mL of hexane and cooled in the refrigerator overnight (ca. 1–2° C., ca. 15 hrs.). 1.77 g (84%) of white crystalline needles were produced whose TLC ($R_f$=0.75 on silica plates developed with 1/1 hexane/ethyl acetate) showed no trace of starting material ($R_f$≈0.10) or of the mono-benzoylated intermediate ($R_f$=0.55): mp 125–127° C.; $^1$H NMR 7.95 (d, 4H), 7.65–7.35 (m, 11H), 4.79–4.67 (q, 4H, $J_{AB}$=13 Hz), 3.29 (s, 1H), trace water at 1.61; IR ca. 3500 $cm^{-1}$ (non-hydrogen bonded OH), ca. 1710 $cm^{-1}$ (aryl ester carbonyl).

2-Phenyl-2-benzyloxy-1,3-dihydroxypropane (6). 2-Phenyl-1,3-dibenzoyloxy-2-hydroxypropane (2.47 g, 7 mmol) was dissolved in 20 mL of anhydrous tetrahydrofuran (THF) under $N_2$. The solution was stirred over a dry ice-acetone bath (ca. −60° C.) while 0.30 g (7.8 mmol) of sodium hydride (NaH) was added as a 60% oil suspension. The mixture was stirred until all of the NaH had dissolved (ca. 30 min while keeping the temperature below −10° C.). The reaction medium was again cooled to ca. −60° C. afterwhich benzylbromide (0.95 mL, 8 mmol) and benzyltributylammonium bromide (0.05 g as catalyst) were added. The cooling bath was removed and the reaction medium stirred overnight (ca. 15 hrs.). The medium was then treated with 5 mL acetic acid, diluted with 50 mL of ethyl acetate and partitioned three times with water (3×10 mL). The organic phase was dried and evaporated under reduced pressure. The residue was chromatographed on a silica gel column (400 mL volume) deploying hexane/ethyl acetate (48/1) as the eluant. Fractions containing material with $R_f$≈0.4 (hexane/ethyl acetate, 4/1)were combined, dried and evaporated. 1.38 g (ca. 42%) of crude, tri-substituted intermediate was obtained whose $^1$H NMR showed an appropriate ratio of aryl to aliphatic protons. This material was then dissolved in 10 mL methanol and treated with ca. 5 mL of 1N NaOH while assuring that the pH was maintained at ca. 10–11. After 2 hours the methanol was evaporated under reduced pressure. The residue was treated with 50 mL of water and then extracted with 50 mL of ethyl acetate. The ethyl acetate solution was partitioned twice with saturated sodium bicarbonate (2×20 mL), twice with water (2×20 mL), dried and evaporated under reduced pressure. The resulting oil (ca. 1.16 g) was chromatographed on a silica gel column (100 mL volume) deploying hexane/ethyl acetate (2/1) as the eluant. Fractions containing material with Rf≈0.3 (hexane/ethyl acetate, 1/1) were combined, dried and concentrated until just turbid. 0.3 g (16% overall) of crystals were obtained upon standing at room temperature (ca. 20° C.): mp 83–86° C.; $^1$H NMR 7.35 (m, 10H), 4.41 (s, 2H), 4.07 (m, 4H); IR ca. 3300 cm$^{-1}$ (brd), no evidence for carbonyl.

We claim:

1. A method for producing 2-substituted glycerol derivatives comprising
   (a) opening a dihydroxyacetone dimer using a composition that protects both liberated 1,3-dihydroxy groups to form di-ether containing ketone monomers, and
   (b) subjecting the di-ether containing ketone monomers to a ketone addition reaction.

2. The method of claim 1, in which the ether forming composition contains trimethylsilylchloride and triethylamine within a nonaqueous, non-protic environment and the addition reaction workup deploys acidic conditions so as to directly produce 2-substituted-1,2,3-tri-hydroxypropanes.

3. The method of claim 2, in which the addition reaction utilizes a Grignard reagent having the formula RMgX.

4. The method of claim 2, in which the addition reaction utilizes a cyanate reagent having the formula NaCN.

5. The method of claim 2, in which the addition reaction utilizes a Reformatsky reagent having the formula XCHR$^1$CO$_2$R$^2$ in combination with Zn.

6. The method of claim 2, in which the addition reaction utilizes a nitroalkane reagent having the formula R$^3$CH$_2$NO$_2$ in combination with a base.

7. The method of claim 3, in which the Grignard reagent is phenylmagnesium bromide.

8. The method of claim 1, in which the ether forming composition contains trimethylsilylchloride and the addition reaction work-up initially avoids acidic conditions so as to produce a partially purified intermediate that is immediately reacted with a benzylhalide followed by an acidic wash to produce 2-substituted-2-benzyloxy-1,3-dihydroxypropane.

9. The method of claim 8, in which the reaction with the benzylhalide uses ØCH$_2$Br and is conducted under anhydrous conditions with sodium hydride as a base or is conducted in a two-phase system with aqueous K$_2$CO$_3$ as a base and a Crown ether present to promote phase-transfer.

10. The method of claim 9, in which the addition reaction utilizes a Grignard reagent having the formula RMgX.

11. The method of claim 9, in which the addition reaction utilizes a cyanate reagent having the formula NaCN.

12. The method of claim 9, in which the addition reaction utilizes a Reformatsky reagent having the formula XCHR$^1$CO$_2$R$^2$ in combination with Zn.

13. The method of claim 9, in which the addition reaction utilizes a nitroalkane reagent having the formula R$^3$CH$_2$NO$_2$ in combination with a base.

14. The method of claim 10, in which the Grignard reagent is phenylmagnesium bromide.

15. The method of claim 2, in which the 2-substitued trihydroxy propanes are immediately reacted with one equivalent of benzylbromide such that the final product becomes a 2-substituted-1-benzyloxy-2,3-dihydroxy derivative of glycerol.

16. The method of claim 2, in which the 2-substituted trihydroxy propanes are immediately reacted with two equivalents of benzylbromide such that the final product becomes a 2-substituted-1,3-dibenzyloxy-2-hydroxy derivative of glycerol.

17. The method of claim 2, in which the 2-substituted trihydroxy propanes are immediately reacted with one equivalent of benzoylchloride such that the final product becomes a 2-substituted -1-benzoyloxy-2,3-dihydroxy derivative of glycerol.

18. The method of claim 2, in which the 2-substituted trihydroxy propanes are immediately reacted with two equivalents of benzoylchloride such that the final product becomes a 2-substituted -1,3-dibenzoyloxy-2-hydroxy derivative of glycerol.

19. The method of claim 17, in which the 2-substituted-1-benzoyloxy-2,3-dihydroxy derivative is immediately reacted with two equivalents of benzylbromide followed by treatment with aqueous sodium hydroxide such that the final product becomes a 2-substituted-1,2-dibenzyloxy-3-hydroxy derivative of glycerol.

20. The method of claim 18, in which the 2-substituted-1,3-dibenzoyloxy-2-hydroxy derivative is immediately reacted with one equivalent of benzylbromide followed by treatment with aqueous sodium hydroxide such that the final product becomes a 2-substituted-2-benzyloxy-1,3-dihydroxy derivative of glycerol.

21. The method of claim 2, in which the addition reaction simultaneously utilizes a family of chemically-related reagents so as to intentionally produce a combinatorial library of products as a mixture whose members all have a 2-substituted tri-hydroxypropane as a chemical scaffold.

22. The method of claim 8, in which the addition reaction simultaneously utilizes a family of chemically-related reagents so as to intentionally produce a combinatorial library of products as a mixture whose members all have a 2-substituted-2-benzyloxy-1,3-dihydroxypropane as a chemical scaffold.

23. The method of claim 15, in which the addition reaction simultaneously utilizes a family of chemically-related reagents so as to intentionally produce a combinatorial library of products as a mixture whose members all have a 2-substituted-1-benzyloxy-2,3-di-hydroxypropane as a chemical scaffold.

24. The method of claim 16, in which the addition reaction simultaneously utilizes a family of chemically-related reagents so as to intentionally produce a combinatorial library of products as a mixture whose members all have a 2-substituted-1,3-dibenzyloxy-2-hydroxypropane as a chemical scaffold.

25. The method of claim 19, in which the addition reaction simultaneously utilizes a family of chemically-related reagents so as to intentionally produce a combinatorial library of products as a mixture whose members all have a 2-substituted-1,2-dibenzyloxy-3-hydroxypropane as a chemical scaffold.

26. The method of claim 20, in which the addition reaction simultaneously utilizes a family of chemically-related reagents so as to intentionally produce a combinatorial library of products as a mixture whose members all have a 2-substituted-2-benzyloxy-1,3-dihydroxypropane as a chemical scaffold.

* * * * *